(12) United States Patent
Ushijima et al.

(10) Patent No.: US 7,763,422 B2
(45) Date of Patent: Jul. 27, 2010

(54) METHOD FOR ASSESSING CANCEROUS STATE

(75) Inventors: Toshikazu Ushijima, Chuo-ku (JP); Atsushi Hagihara, Koto-ku (JP)

(73) Assignees: Sumitomo Chemical Company, Limited, Tokyo (JP); Japan as Represented by President of National Cancer Center, Tokyo (JP)

( * ) Notice: Subject to any disclaimer, the term of this patent is extended or adjusted under 35 U.S.C. 154(b) by 649 days.

(21) Appl. No.: 10/572,352

(22) PCT Filed: Sep. 15, 2004

(86) PCT No.: PCT/JP2004/013871

§ 371 (c)(1),
(2), (4) Date: Nov. 2, 2006

(87) PCT Pub. No.: WO2005/026350

PCT Pub. Date: Mar. 24, 2005

(65) Prior Publication Data

US 2007/0135366 A1 Jun. 14, 2007

(30) Foreign Application Priority Data

Sep. 16, 2003 (JP) ............................. 2003-322822

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search ...................... 435/6; 536/23.1, 24.3
See application file for complete search history.

(56) References Cited

FOREIGN PATENT DOCUMENTS

WO 2003/076594 A 9/2003

OTHER PUBLICATIONS

Zhang et al. , Structure and Expression of Fibrillin-2, A novel microfibrillar component preferentially located in elastic matrices. The Journal of Cell Biology 124(5) : 855-863 (1994).*
Herman et al., Methylation-specific PCR : A novel PCR assay for methylation styatus of CpG islands PNAs 93 : 9821-9826 (1996).*
Esteller et al. Cancer Research 61 : 3225-3229 (2001).*
Gerdes et al., p16INK4a alterations in chronic pancreatitis—indicator for high-risk lesions for pancreatic cancer. Surgery 129 : 490-497 (2001).*
Jensen et al., Cancer Biology & Therapy 1 (3) : 293-296 (2002).*
Salz et al., PNAS 86 : 2602-2606 (1989).*
Ueki et al., Cancer Research 60 : 1835-1839 (2000).*
Zhang et al., The Journal of Cell Biology 124 (5) : 855-863 (1994).*
Sato et al., Cancer Research 63 : 3735-3742 (2003).*
M. Jansen et al., "Aberrant methylation of the 5' CpG island of TSLC1 is common in pancreatic ductal adenocarcinoma and is first manifest in high-grade Pan1Ns,", *Cancer Biol. Ther.*, vol. 1, No. 3, 2002, pp. 293-296.
T. Ueki et al., "Hypermethylation of multiple genes in pancreatic adenocarcinoma", *Cancer Res.*, vol. 60, No. 7, 2000, pp. 1835-1839.
M. Esteller et al., "A gene hypermethylation profile of human cancer", *Cancer Res.*, vol. 61, No. 8, 2001, pp. 3225-3229.
H. Zhang et al., "Structure expression of fibrillin-2, a novel microfibrillar component preferentially located in elastic matrices," *The Journal of Cell Biology*, vol. 124, No. 5, 1994, pp. 855-863.
Sato N., et al. "Discovery of novel targets for aberrant methylation in pancreatic carcinoma using high-throughput microarrays," Cancer Research, vol. 63, No. 13, pp. 3735-3742 (Jul. 1, 2003).
Hagihara A., et al. "Identification of 27 5' CpG islands aberrantly methylated and 13 genes silenced in human pancreatic cancers," Oncogene, vol. 23, No. 53, pp. 8705-8710 (Nov. 11, 2004).

* cited by examiner

*Primary Examiner*—Ethan Whisenant
(74) *Attorney, Agent, or Firm*—Sughrue Mion, PLLC

(57) ABSTRACT

The present invention relates to a method for assessing a cancerous state of a mammal-derived specimen, which comprises:

Figure 1:
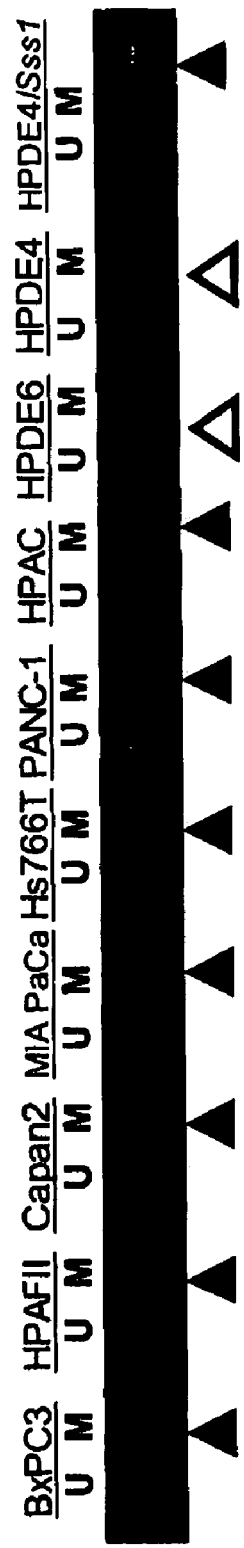

(1) a first step of measuring a methylation frequency of Fibrillin2 gene contained in a mammal-derived specimen or an index value having the correlation therewith, and (2) a second step of determining a cancerous state of the specimen based on a difference obtained by comparing the measured methylation frequency or the index value having the correlation therewith, with a control; and the like.

19 Claims, 4 Drawing Sheets

METHOD FOR ASSESSING CANCEROUS STATE

TECHNICAL FIELD

The present invention relates to a method for assessing a cancerous state of a mammal-derived specimen, and the like.

BACKGROUND ART

Although it has been gradually revealed that a cancer is a disease, a cause of which is gene abnormality, the mortality of cancer patients is still high, demonstrating that diagnosing methods and treating methods which are currently available are not necessarily fully satisfactory. It is clinically significant to detect cancer early and to choose an effective treatment for the detected cancer and further to provide aftercare for checking cancer recurrence and the like following treatment.

Then, there is desired development of a method for assessing a cancerous state of a mammal-derived specimen based on detection of a gene abnormality, which is suitable for a diagnosing method to detect cancer early, an efficacy assessment of cancer treatment and check of cancer recurrence and the like.

DISCLOSURE OF THE INVENTION

Under such the circumstances, the present inventors intensively studied and, as a result, have found that a Fibrillin2 gene (hereinafter, referred to as FBN2 gene in some cases) is methylated in a cancer cell line and a specimen of a cancer tissue at a significantly higher frequency as compared with an immortalized normal cell line and a specimen of a normal tissue and, in this cancer cell line, the expression level of Fibrillin2 gene in a cancer cell line is significantly lower as compared with an immortalized normal cell line and, further, have found that the expression level of such the gene can be increased by acting a DNA methylation inhibitor on the cancer cell line, which resulted in completion of the present invention.

That is, the present invention provides:

1. a method for assessing a cancerous state of a mammal-derived specimen, which comprises:

(1) a first step of measuring a methylation frequency of Fibrillin2 gene contained in a mammal-derived specimen or an index value having the correlation therewith, and (2) a second step of determining a cancerous state of the specimen based on a difference obtained by comparing the measured methylation frequency or the index value having the correlation therewith, with a control (hereinafter, referred to as present assessing method in some cases);

2. the assessing method according to the above 1, wherein the mammal-derived specimen is cells;

3. the assessing method according to the above 1, wherein the mammal-derived specimen is a tissue;

4. a method for assessing a cancerous state of a mammal-derived specimen, which comprises:

(1) a first step of measuring a methylation frequency of Fibrillin2 gene contained in the mammal-derived specimen, and (2) a second step of determining a cancerous state of the specimen based on a difference obtained by comparing the measured methylation frequency with a control;

5. the assessing method according to the above 1, wherein the mammal-derived specimen is cells, and the cancerous state of the specimen is a malignancy of mammal-derived cells;

6. the assessing method according to the above 4, wherein the mammal-derived specimen is cells, and the cancerous state of the specimen is a malignancy of a mammal-derived cell;

7. the assessing method according to the above 1, wherein the mammal-derived specimen is a tissue, and the cancerous state of the specimen is an amount of cancer cells existing in a mammal-derived tissue;

8. the assessing method according to the above 4, wherein the mammal-derived specimen is a tissue, and the cancerous state of the specimen is an amount of cancer cells existing in a mammal-derived tissue;

9. the assessing method according to the above 8, wherein the tissue is a pancreatic tissue, and the cancer is pancreatic cancer:

10. the assessing method according to the above 1 or 4, wherein the methylation frequency of a gene is a methylation frequency of cytosine in one or more nucleotide sequence(s) represented by 5'-CG-3' present in a nucleotide sequence of a promoter region, an untranslated region or a translated region of the gene;

11. the assessing method according to the above 12, wherein the tissue is a pancreatic tissue, and the cancer is pancreatic cancer;

12. the assessing method according to the above 1 or 4, wherein the methylation frequency of a gene is a methylation frequency of cytosine in one or more nucleotide sequence(s) represented by 5'-CG-3' present in a nucleotide sequence of a promoter region in the gene;

13. the assessing method according to the above 1 or 4, wherein the methylation frequency of a gene is a methylation frequency of cytosine in one or more nucleotide sequence(s) represented by 5'-CG-3' present in a nucleotide sequence of an untranslated region or a translated region of the gene;

14. the assessing method according to the above 1, wherein the methylation frequency of a gene is a methylation frequency of cytosine in one or more nucleotide sequence(s) represented by 5'-CG-3' present in the nucleotide sequence represented by SEQ ID No: 1;

15. the assessing method according to the above 16, wherein the tissue is a pancreatic tissue, and the cancer is pancreatic cancer;

16. a method for assessing a cancerous state of a mammal derived specimen, which comprises:

(1) a first step of measuring an index value having the correlation with a methylation frequency of Fibrillin2 gene contained in the mammal-derived specimen, and (2) a second step of determining a cancerous state of the specimen based on a difference obtained by comparing the index value having the correlation with the measured methylation frequency with a control;

17. the assessing method according to the above 16, wherein the index value having the correlation with a methylation frequency of Fibrillin2 gene is an amount of an expression product of the Fibrillin2 gene;

18. the assessing method according to the above 17, wherein the amount of an expression product of Fibrillin2 gene is an amount of a transcription product of the gene;

19. the assessing method according to the above 17, wherein the amount of an expression product of Fibrillin2 gene is an amount of a translation product of the gene;

20. a method for searching a substance having the ability of promoting the expression of Fibrillin2 gene, which comprises:

(1) a first step of bringing a test substance into contact with a cancer cell, (2) a second step of measuring an amount of an expression product of Fibrillin2 gene contained in the cancer cell after the first step (1), and (3) a third step of determining the ability of the test substance to promote the expression of Fibrillin2 gene possessed by, based on a difference obtained by comparing the measured amount of an expression product with a control (hereinafter, referred to as present searching method in some cases);

21. the searching method according to the above 20, wherein the cancer cell is pancreatic cancer cell;

22. an anti-cancer agent, which comprises a substance having the ability found by the searching method of the above 20 as an active ingredient, wherein the active ingredient is formulated into a pharmaceutically acceptable carrier;

23. an anti-cancer agent, which comprises a nucleic acid comprising a nucleotide sequence encoding an amino acid sequence of Fibrillin2 as an active ingredient, wherein the active ingredient is formulated into a pharmaceutically acceptable carrier;

24. use of methylated Fibrillin2 gene as a cancer marker;

25. the use according to the above 24, wherein the cancer marker is a pancreatic cancer marker;

26. a method for inhibiting canceration, which comprises a step of administering a substance which reduces a methylation frequency of Fibrillin2 gene, to cells in a body of a mammal which can be diagnosed as a cancer; and 27. the canceration inhibiting method according to the above 26, wherein the cancer is pancreatic cancer, and the like.

BRIEF DESCRIPTIONS OF THE DRAWINGS

FIG. 1 is a view showing the results obtained by performing PCR using, as a template, genomic DNAs prepared from human-derived immortal (normal) pancreatic ductal epithelial cell lines (HPDE-4/E6E7 and HPDE6-E6E7c7) and seven kinds of pancreatic cancer cell lines (BXPc3, HPAF-II, Capan-2, MiaPaCa-2, Hs766T, PANC-1 and HPAC) and treated with sodium bisulfite, respectively, and analyzing the PCR reaction solutions after FCR with agarose gel electrophoresis. Names of cells used are shown at the top of the view. The view indicated as HPDE4/SssI shows DNA obtained by treatment of genomic DNAs of HPDE-4/E6E7 with methylase SssI. Lane U, the PCR reaction solution of PCR using a methylation-specific primer; lane M, the PCR reaction solution of PCR using a methylation-specific primer.

Figure 2:
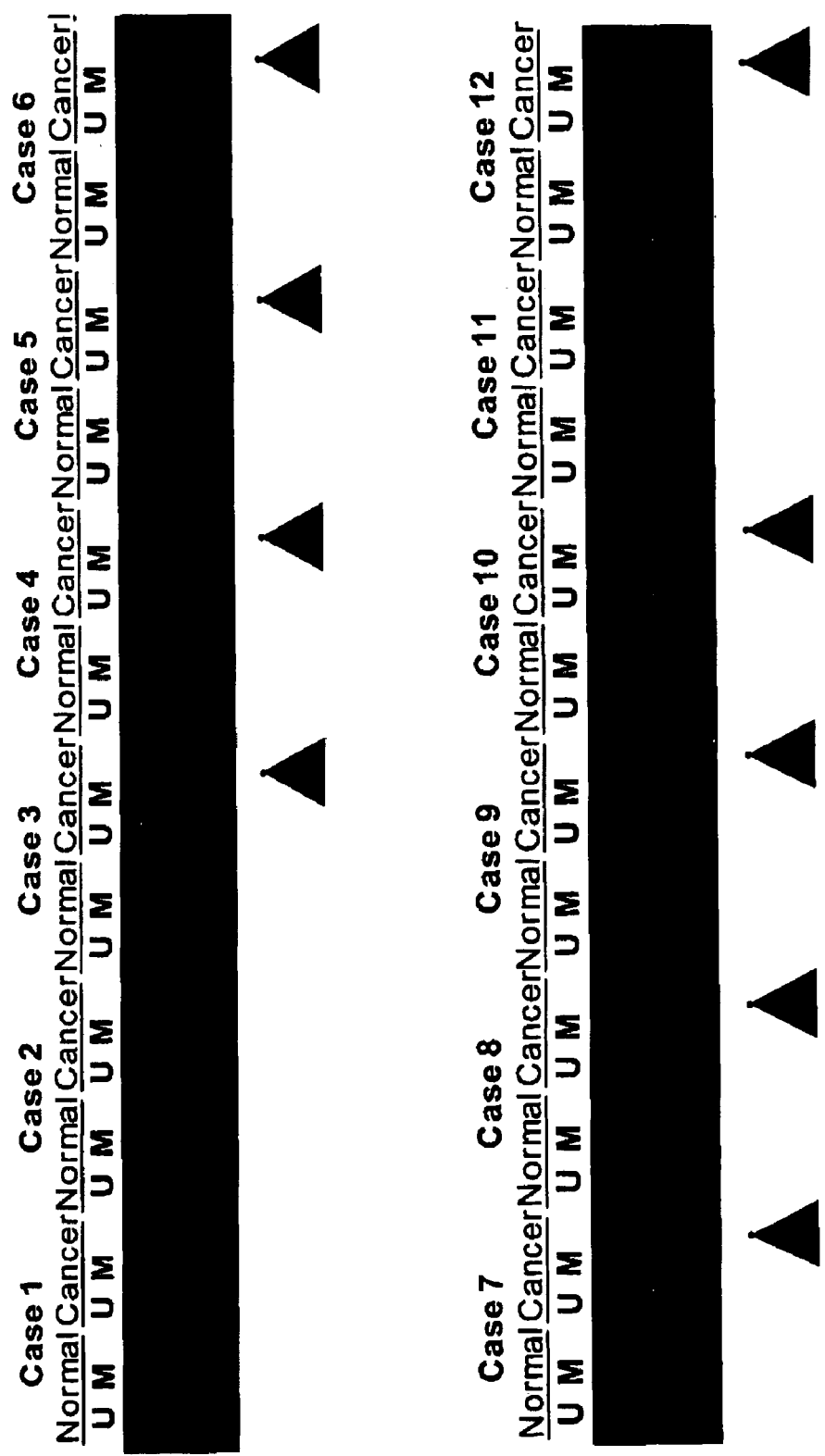

FIG. 2 is a view showing the results obtained by performing PCR using, as a template, genomic DNAs prepared from 12 specimens of pancreatic cancer tissues and the surrounding pancreatic normal tissues (obtained from patients with their informed consent) and treated with sodium bisulfite, respectively, and analyzing the PCR reaction solutions after PCR with agarose gel electrophoresis. Case 1 to case 12 represent specimens. Cancer represents pancreatic cancer tissue and Normal represents the surrounding pancreatic normal tissue. Lane U, the PCR reaction solution of PCR using a methylation-specific primer; lane M, the PCR reaction solution of PCR using a methylation-specific primer.

Figure 3:
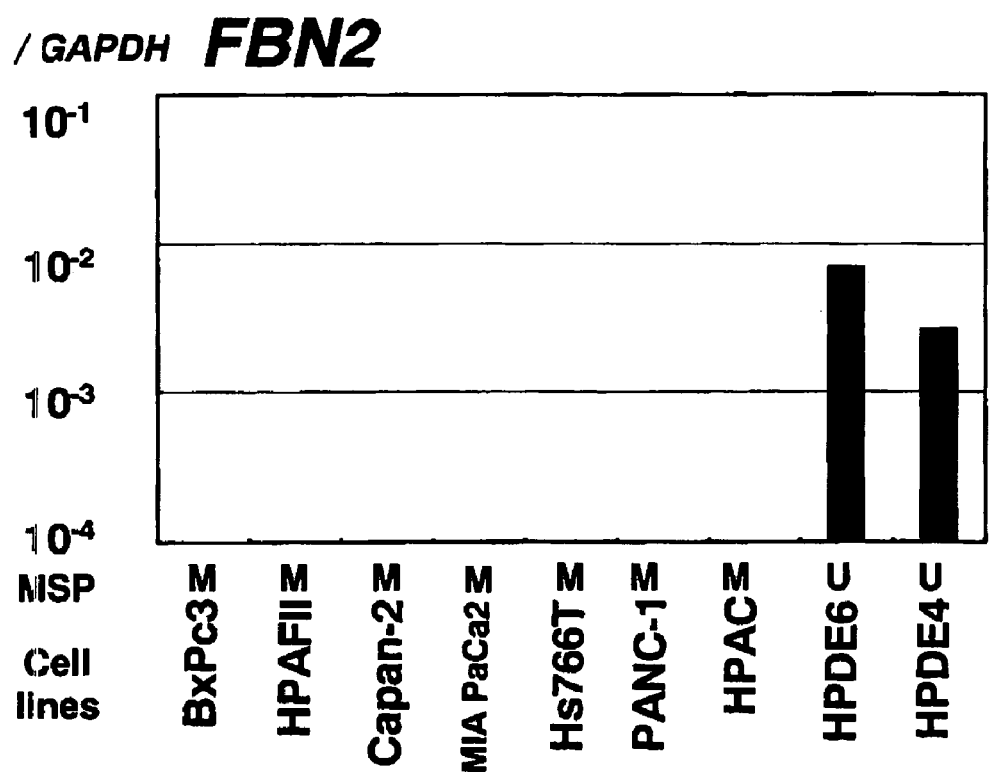

FIG. 3 is a view showing Fibrillin2 gene dosage obtained by amplifying with Real Time PCR DNA derived from mRNA of Fibrillin2 gene in seven kinds of human-derived pancreatic cancer cell lines (BXPc3, HPAF-II, Capan-2, MiaPaCa-2, Hs766T, PANC-1 and HPAC) and immortal (normal) pancreatic ductal epithelial cells lines (HPDE-4/E6E7 and HPDE6-E6E7c7). Names of cells used are shown at the bottom of the view. The vertical axis represents Fibrillin2 gene dosage divided by GAPDH gene dosage.

Figure 4:
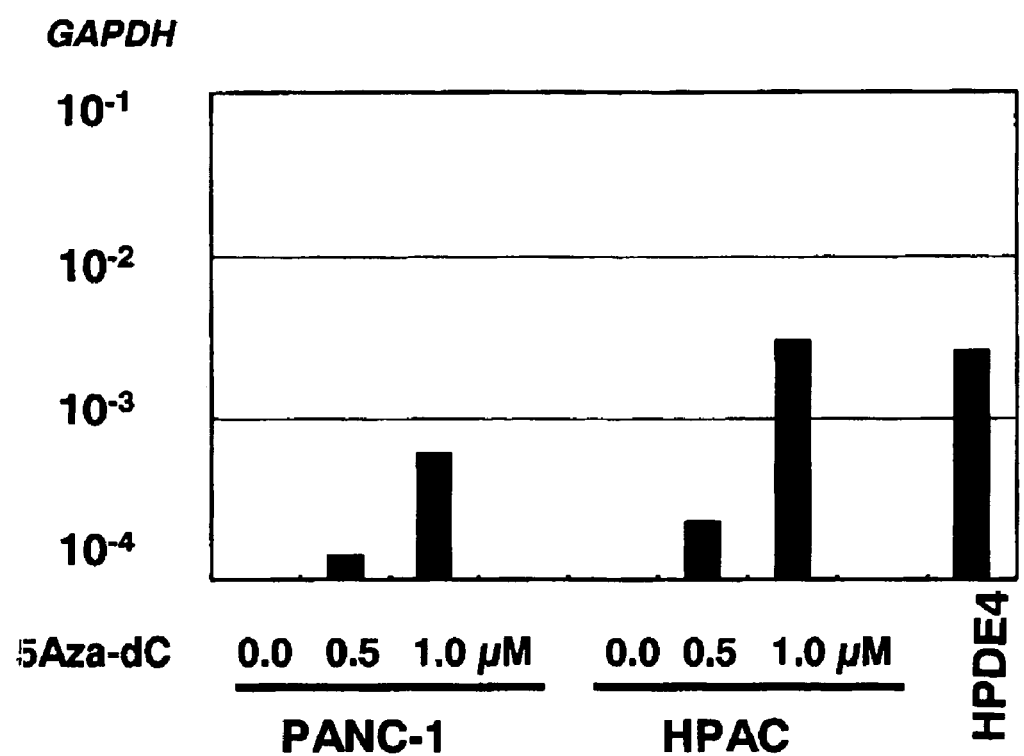

FIG. 4 is a view showing Fibrillin2 gene dosage obtained by amplifying with Real Time PCR DNA derived from mRNA of Fibrillin2 gene in 2 kinds of pancreatic cancer cell lines (PANC-1 and HPAC) to which a methylation inhibitor 5 Aza-dC was applied in the concentration of 0, 0.5 μM or 1 μM, and in immortal (normal) pancreatic ductal epithelial cell (HPDE-4/E6E7). Names of cells used are shown at the bottom of the view. The vertical axis represents Fibrillin2 gene dosage divided by GAPDH gene dosage.

BEST MODE FOR CARRYING OUT THE INVENTION

The present invention will be explained in detail below.

The present invention relates to use of methylated Fibrillin2 gene as a cancer marker (e.g. pancreatic cancer marker or the like), and the like.

Examples of Fibrillin2 gene used as a marker gene in the present invention include a human-derived gene containing an untranslated region (non-coding region) and a translated region (coding region) of Fibrillin2 gene and a promoter region located on a 5' upstream side thereof. A nucleotide sequence of human-derived Fibrillin2 gene and an amino acid sequence encoded by it are described, for example, in Genbank Accession No. NM_001999 and the like. A nucleotide sequence of a genomic DNA, containing an exon located on a 5' most-upstream side (hereinafter, referred to as exon 1) among exons which comprise an untranslated region and a translated region (coding region) of human-derived Fibrillin2 gene, is described, for example, in Genbank Accession No. AC113387 and the like. In a nucleotide sequence described in Genbank Accession No. AC113387, for example, a nucleotide sequence of the exon 1 of human-derived Fibrillin2 gene is shown by nucleotide numbers 119656 to 119910. The Fibrillin2 gene utilized in the present invention includes, in addition to a gene having the known nucleotide sequence aforementioned, a gene having a nucleotide sequence such as deletion, substitution or addition of a nucleotide has occurred in such the nucleotide sequence, deriving from a naturally occurring mutation due to a difference in organism species, a difference between individuals, or a difference between organs or tissues, or the like.

There is the phenomenon that, among four kinds of bases constituting a gene (genomic DNA), only cytosine is methylated in mammals. For example, in mammal-derived Fibrillin2 gene, some of cytosines of a genomic DNA of the gene are methylated. And, methylation modification of DNA is limited to cytosines in a nucleotide sequence represented by 5'-CG-3' (C represents cytosine, and G represents guanine; hereinafter, the nucleotide sequence is referred to as CpG in some cases). In cytosine, a site to be methylated is a 5-position thereof. Upon DNA replication prior to cell division, only cytosine in CpG of a template chain is methylated immediately after replication, but cytosine in CpG of a newly produced chain is also quickly methylated by the action of methyltransferase. Therefore, the status of methylation of DNA is inherited as it is to new two sets of DNAs also after DNA replication.

In the first step of the present assessing method, a "methylation frequency" is represented, for example, by a ratio of haploids in which the cytosine is methylated, when the presence or the absence of methylation of cytosine in CpG to be investigated, is investigated for plural haploids.

Further, in the first step of present assessing method, examples of an "index value having the correlation with a (methylation frequency)" include an amount of an expression product of Fibrillin2 gene (more specifically, an amount of a transcription product of the gene, and an amount of a translation product of the gene) and the like. In the case of such the amount of an expression product, there is such the negative correlation that as the methylation frequency grows higher, the amount decreases accordingly.

Examples of the mammal-derived specimen in the first step of the present assessing method include living body samples such as cancer cells such as pancreatic cancer cells or a tissue containing it, and cells potentially containing a DNA derived from cancer cells such as pancreatic cancer cells, a tissue containing it (herein, a tissue broadly means including body fluids such as blood, plasma, serum, lymph and the like; lymph rode and the like) or living body secreted substances (urine, milk and the like). Specifically, for example, when the cancer is pancreatic cancer, examples include pancreatic tissue (including pancreatic fluid) taken from a subject animal.

These living body samples may be used as it is as a specimen, or living body samples prepared by various procedures such as separation, fractionation, immobilization and the like from such the living body samples may be used as a specimen.

When the mammal-derived specimen is blood, the present assessing method can be expected to be utilized in periodic physical checking, simple test, and the like.

In the first step of the present assessing method, a method for measuring a methylation frequency of Fibrillin2 gene contained in a mammal-derived specimen or an index value having the correlation therewith may be performed, for example, as follows.

As a first method, there is a method in which, specimen-derived DNA is contacted with a reagent which modifies unmethylated cytosine and, thereafter, a polymerase chain reaction (hereinafter, referred to as PCR) is performed using the DNA as a template and using primers which can recognize the presence or the absence of methylation of cytosine to be analyzed, and an amount of the resulting amplification product is investigated.

A DNA is first extracted from a mammal-derived specimen, for example, using a commercially available DNA extracting kit or the like.

When blood is used as a specimen, plasma or serum is prepared from the blood according to the conventional method, and free DNA (including a DNA derived from cancer cells such as pancreatic cancer cells and the like) contained in the prepared plasma or serum as a specimen is analyzed, whereby, a DNA derived from cancer cells such as pancreatic cancer cell can be analyzed while avoiding a hemocyte-derived DNA, and a sensitivity for detecting cancer cell such as pancreatic cancer cell, or a tissue containing it can be improved.

Then, after the extracted DNA is contacted with a reagent which modifies unmethylated cytosine, PCR is performed using the DNA as a template and using primers which can recognize the presence or the absence of methylation of cytosine to be analyzed, and an amount of the resulting amplification product is investigated. Cytosine to be analyzed may be selected from among cytosines in one or more nucleotide sequence(s) represented by 5'-CG-3' which is present in a nucleotide sequence of a promoter region, an untranslated region or a translated region (coding region) of Fibrillin2 gene.

Herein, for example, examples of one or more nucleotide sequence(s) represented by CpG which is present in a nucleotide sequence of a promoter region or an untranslated region or a translated region (coding region) of Fibrillin2 gene include a nucleotide sequence of a genomic DNA containing an exon 1 of human-derived Fibrillin2 gene and a promoter region located on a 5' upstream side thereof, more specifically, the nucleotide sequence represented by SEQ ID NO: 1 (corresponding to a sequence complementary to the nucleotide sequence represented by nucleotide numbers 118801 to 121000 of a nucleotide sequence described in Genbank Accession No. AC113387). In the nucleotide sequence represented by SEQ ID NO: 1, the nucleotide sequence of the exon 1 is shown by nucleotide numbers 1091 to 1345. Cytosine in a nucleotide sequence represented by CpG which is present in the nucleotide sequence represented by SEQ ID NO: 1 shows a high methylation frequency (i.e. hypermethylation), for example, in cancer cells such as pancreatic cancer cells. More specifically, examples of cytosine having a high methylation frequency in a pancreatic cancer cell include cytosines represented by nucleotide numbers 679, 687, 690, 699, 746, 773, 777, 783, 795, 799, 812, 823, 830, 834, 843 and the like in the nucleotide sequence of SEQ ID NO: 1.

As a reagent for modifying unmethylated cytosine, for example, bisulfite such as sodium bisulfite can be used. Incidentally, in principle, a reagent which specifically modify only methylated cytosine can also be used.

In order that the extracted DNA is contacted with a reagent for modifying unmethylated cytosine, for example, after the DNA is first denaturated in an alkaline solution (pH 9 to 14), the DNA is treated with bisulfite such as sodium bisulfite (concentration in a solution: e.g. final concentration 3M) at 55° C. for around about 10 to 16 hours (overnight). Denaturation at 95° C. and reaction at 50° C. may be repeated 10 to 20 times to accelerate the reaction. In this case, unmethylated cytosine is converted into uracil and, on the other hand, methylated cytosine is not converted into uracil, but still remains as cytosine.

Then, PCR using a DNA treated with bisulfite or the like as a template, and using one pair of methylation-specific primers, each selected from a nucleotide sequence when methylated cytosine is contained in the nucleotide sequence in which cytosine at a position to be methylated (cytosine in CpG) still remains as cytosine, and unmethylated cytosine (cytosine not contained in CpG) is converted into uracil and a nucleotide sequence complementary to such the nucleotide sequence (hereinafter, also referred to as methylation-specific PCR in some cases), and PCR using a DNA treated with bisulfite as a template, and using one pair of unmethylation-specific primers, each selected from a nucleotide sequence when cytosine is not methylated (nucleotide sequence in which all cytosines are converted into uracil) and a nucleotide sequence complementary to such the nucleotide sequence (hereinafter, also referred to as unmethylation-specific PCR in some cases) are performed.

In the aforementioned PCR, in the case of PCR using the methylation-specific primer (former), a DNA in which cytosine to be analyzed is methylated is amplified and, on the other hand, in the case of PCR using the unmethylation-specific primer (latter), a DNA in which cytosine to be analyzed is not methylated is amplified. By comparing amounts of these amplification products, the presence or the absence of methylation of cytosine to be analyzed is investigated. Like this, a methylation frequency can be measured.

Herein, in view of that, in the methylation-specific primer, cytosine which has not undergone methylation is converted into uracil, and cytosine which has undergone methylation is not converted into uracil, as primers, a PCR primer specific for a nucleotide sequence containing cytosine which has undergone methylation (methylation-specific primer) is designed, and a PCR primer specific for a nucleotide sequence containing cytosine which has not undergone methylation (unmethylation-specific primer) is designed. Since design is performed based on a DNA chain which has been chemically converted by sulfite treatment and has become not complementary, based on respective chains of DNAs which were originally double-stranded, a methylation specific primer and a unmethylation-specific primer may be also prepared from respective chains. In order to enhance specificity for methyl or non-methyl, such the primers are preferably designed so that primers contain cytosine in CpG near a 3'-terminal of primers. Moreover, in order to make analysis easy, one of primers may be labeled.

More specifically, a primer for measuring a methylation frequency of Fibrillin2 gene with methylation-specific PCR can be designed as described above, for example, based on a nucleotide sequence containing one or more cytosine(s) in CpG present in a nucleotide sequence in a promoter region, an untranslated region or a translated region (coding region) of Fibrillin2 gene. For example, design can be performed based on a nucleotide sequence containing one or more cytosine(s) in CpG present in the nucleotide sequence represented by SEQ ID NO: 1, more specifically, cytosine(s) represented by nucleotide numbers 679, 687, 690, 699, 746, 773, 777, 783, 795, 799, 812, 823, 830, 834, 843 and the like in the nucleotide sequence represented by SEQ ID NO: 1. Examples of such the primers are shown below.

```
<Unmethylation-specific primer>
U1:  5'-TATGGGAATTTGTTGAGTTTTGT-3'   (SEQ ID No: 2)
U2:  5'-AACCAACAACCCCAAACA-3'        (SEQ ID No: 3)

<Methylation-specific primer>
M1:  5'-GGGAATTCGTCGAGTTTTGC-3'      (SEQ ID No: 4)
M2:  5'-AACCGACAACCCCGAACG-3'        (SEQ ID No: 5)
```

Examples of a reaction solution in the methylation-specific PCR include a reaction solution obtained by mixing 50 ng of a DNA to be a template, each 1 μl of 10 pmol/μl of each primer solution, 4 μl of 2.5 mM DNTP, 2.5 μl of 10× buffer (100 mM Tris-HCl pH 8.3, 500 mM KCl, 20 mM $MgCl_2$), and 0.2 μl of 5 U/μl thermostable DNA polymerase, and adding sterilized ultrapure water to an amount of 25 μl. Examples of reaction conditions include the condition under which the aforementioned reaction solution is retained at 95° C. for 10 minutes and, thereafter, 30 to 40 cycles of temperature maintenance is performed, each cycle being 30 seconds at 95° C., then 30 seconds at 55 to 65° C. and 30 seconds at 72° C.

After such the PCR is performed, amounts of the resulting amplification products are compared. For example, in the case of an analyzing method which can compare amounts of respective amplification products obtained by PCR using the methylation-specific primer and PCR using the unmethylation-specific primer (denatured polyacrylamide gel electrophoresis or agarose gel electrophoresis), a gel after electrophoresis is put on DNA-staining to detect bands of amplification products, and density of the detected bands are compared. Herein, using pre-labeled primers in place of DNA-staining, the density of bands may be compared using the label as an index. In cases where quantitative determination is required, amounts of the respective products may be compared by using Real Time PCR which is a PCR method capable of high-accuracy quantitation such that slight difference in gene dosage of about twice can be detected by real-time monitoring of PCR reaction product and analyzing kinetics. Methods of performing Real Time PCR include, for example, a method using a probe such as template-directed nucleic acid polymerase probe and a method using an intercalator such as SYBR Green. As apparatus and reagents for Real Time PCR, commercially available apparatus and reagents can be used.

Such the method is the method which is generally also called methylation-specific PCR and was reported by Herman (Herman et al., Proc. Natl. Acad. Sci USA, 93, 9821-9826, 1996), and this method utilizes a difference in the chemical property between cytosine and 5-methylcytosine.

As a second method, there is a method in which, specimen-derived DNA is contacted with a reagent which modifies unmethylated cytosine and, thereafter, using the DNA as a template, DNA containing cytosine to be analyzed is amplified by PCR and a nucleotide sequence of the resulting amplification product is directly analyzed.

A DNA is first extracted from a mammal-derived specimen, for example, using a commercially available DNA extracting kit or the like.

When blood is used as a specimen, plasma or serum is prepared from the blood according to the conventional method, and a free DNA (including a DNA derived from cancer cells such as pancreatic cancer cells) contained in the prepared plasma or serum as a specimen is analyzed, thereby, a DNA derived from cancer cells such as pancreatic cancer cells can be analyzed while avoiding a hemocyte-derived DNA, and a sensitivity for detecting cancer cells such as pancreatic cancer cells, or a tissue or the like containing it can be improved.

Then, the extracted DNA is contacted with a reagent for modifying unmethylated cytosine, and using the DNA as a template, DNA containing cytosine to be analyzed is amplified by performing PCR using primers which are designed as described below based on a nucleotide sequence containing cytosine in one or more nucleotide sequence(s) represented by CpG which is present in a nucleotide sequence of a promoter region, untranslated region or a translated region (coding region) of Fibrillin2 gene, and a nucleotide sequence of the resulting amplification product is directly analyzed.

Herein, examples of one or more nucleotide sequence(s) represented by CpG present in a nucleotide sequence of a promoter region, untranslated region or a translated region (coding region) of Fibrillin2 gene include a nucleotide sequence of a genomic DNA containing an exon 1 of human-derived Fibrillin2 gene and a promoter region located on a 5' upstream side thereof, more specifically, the nucleotide sequence represented by SEQ ID NO: 1 (corresponding to a sequence complementary to the nucleotide sequence represented by nucleotide numbers 118801 to 121000 of a nucleotide sequence described in Genbank Accession No. AC113387). In the nucleotide sequence represented by SEQ ID NO: 1, the nucleotide sequence of the exon 1 is shown by nucleotide numbers 1091 to 1345. Cytosine in a nucleotide sequence represented by CpG present in the nucleotide sequence represented by SEQ ID NO: 1, inter alia, cytosine in CpG present in a region in which CpGs are densely present in the nucleotide sequence represented by SEQ ID NO: 1 shows a high methylation frequency (i.e. hypermethylation status) in cancer cells such as pancreatic cancer cells. More specifically, examples of cytosine having a high methylation frequency in a pancreatic cancer cell include cytosines represented by nucleotide numbers 679, 687, 690, 699, 746, 773, 777, 783, 795, 799, 812, 823, 830, 834, 843 and the like in the nucleotide sequence of SEQ ID NO: 1.

As a primer used in the PCR, it is better to design a pair of primers which can amplify a DNA having a nucleotide sequence containing the cytosine, based on a nucleotide sequence of a 5' upstream side of cytosine to be analyzed and a nucleotide sequence of 3' downstream side thereof. A nucleotide sequence for primer design is selected so that it does not contain cytosine in CpG to be analyzed. And, when a nucleotide sequence selected for primer design does not contain cytosine at all, a selected nucleotides sequence and a nucleotide sequence complementary to such the nucleotide sequence can be employed as they are, respectively, as a nucleotide sequence for a primer. In addition, when a nucleotide sequence selected for primer design contains cytosine other than that to be analyzed, but the cytosine is not cytosine in CpG, a primer is designed in view of that these cytosines are converted into uracil. That is, one pair of primers, each having a nucleotide sequence in which all cytosines are converted into uracil and a nucleotide sequence complementary to such the nucleotide sequence is designed. Further, when a nucleotide sequence selected for primer design contains cytosine other than that to be analyzed, and the cytosine is cytosine in CpG, primers are designed in view of that cytosine which has not undergone methylation is converted into uracil, and cytosine which has undergone methylation is not converted into uracil. That is, one pair of methylation specific primers, respectively, selected from a nucleotide sequence which contains methylated cytosine [a nucleotide sequence in which cytosine at a position to be methylated (cytosine in CpG) still remains as cytosine, and unmethylated cytosine (cytosine not contained in CpG) is converted into uracil] and a nucleotide sequence complementary to such the nucleotide sequence, and one pair of unmethylation-specific primers, each having a nucleotide sequence in which cytosine is not methylated (a nucleotide sequence in which all cytosines are converted into uracils) and a nucleotide sequence complementary to such the nucleotide sequence are designed. In this case, equivalent amounts of the methylation-specific primer pair and the unmethylation-specific primer pair are used in the aforementioned PCR, by mixing them.

As a reagent for modifying unmethylated cytosine, for example, bisulfite such as sodium bisulfite can be used. Incidentally, in principle, a reagent which specifically modify only methylated cytosine can also be used.

In order that the extracted DNA is contacted with a reagent for modifying unmethylated cytosine, for example, the DNA is first treated with bisulfite such as sodium bisulfite (concentration in a solution: for example, the final concentration 3M) at 55° C. for around about 10 to 16 hours (overnight) in an alkaline solution (pH 9 to 14). Denaturation at 95° C. and reaction at 50° C. may be repeated 10 to 20 times to accelerate the reaction. In this case, unmethylated cytosine is converted into uracil and, on the other hand, methylated cytosine is not converted into uracil, and still remains as cytosine.

Then, PCR is performed using a DNA treated with bisulfite or the like as a template, and using primers which are designed as described above. Nucleotide sequences of the resulting amplification products are compared, and a methylation frequency can be measured by the comparison.

More specifically, primers for measuring a methylation frequency of Fibrillin2 gene by direct analysis of a nucleotide sequence can be designed as described above, for example, based on a nucleotide sequence containing one or more cytosine(s) in CpG present in a nucleotide sequence which is in a promoter region, untranslated region or a translated region (coding region) of the Fibrillin2 gene. For example, primers can be designed to analyze cytosine(s) in CpG present in the nucleotide sequence represented by SEQ ID NO: 1, specifically, one or more cytosine(s) represented by nucleotide numbers 1499, 1501, 1525, 1535, 1539, 1555, 1566, 1569, 1595, 1599, 1606, 1619, 1621, 1626, 1647, 1650, 1657, and 1669 in the nucleotide sequence represented by SEQ ID NO: 1. For example, by using primers B1 and B2 shown below, DNA (251 bp) is amplified, said DNA comprising a nucleotide sequence arising from bisulfite treatment of DNA which had comprised the nucleotide sequence represented by nucleotide numbers 1442 to 1692 in the nucleotide sequence represented by SEQ ID NO: 1. The primer pair can be used as primers to investigate methylation frequency of cytosine (s) represented by nucleotide numbers 1499, 1501, 1525, 1535, 1539, 1555, 1566, 1569, 1595, 1599, 1606, 1619, 1621, 1626, 1647, 1650, 1657, and 1669 in the nucleotide sequence represented by SEQ ID NO: 1.

```
<primer>
B1:  5'-TAGTTGGAGTTTAGAGTTGTA-3'    (SEQ ID No: 6)

B2:  5'-CTTCTCTAACCCCTACAAC-3'      (SEQ ID No: 7)
```

Examples of a reaction solution in PCR include a reaction solution obtained by mixing 25 ng of a DNA as a template, each 1 µl of four kinds of 20 pmol/µl respective primer solutions, 3 µl of 2 mM DNTP, 2.5 µl of 10× buffer (100 mM Tris-HCl pH 8.3, 500 mM KCl, 20 mM $MgCl_2$) and 0.2 µl of 5 U/µl thermostable DNA polymerase, and adding sterilized ultrapure water to this to an amount of 25 µl. Examples of the reaction conditions include the condition in which the aforementioned reaction solution is retained at 95° C. for 10 minutes and, thereafter, 30 to 40 cycles of temperature maintenance is performed, one cycle being 30 seconds at 95° C., then 30 seconds at 51° C., and further 30 seconds at 72° C.

After such the PCR is performed, nucleotide sequences of the resulting amplification products are compared, and a methylation frequency is measured from the comparison.

That is, by directly analyzing nucleotide sequences of the amplification products, whether a base at a position corresponding to cytosine to be analyzed is cytosine or thymine (uracil) is determined. By comparing an area of a peak showing cytosine and an area of a peak showing thymine (uracil) both detected at a position corresponding to cytosine to be analyzed in a chart of peaks showing nucleotides in the resulting amplification products, a methylation frequency of cytosine to be analyzed can be measured. Alternatively, as a method for directly analyzing a nucleotide sequence, after the amplification products obtained by the PCR are once cloned using *Escherichia coli* or the like as a host, DNAs which are cloned respectively into plural clones are prepared, and nucleotide sequences of the DNAs may be analyzed. By obtaining a ratio of samples in which a base detected at a position corresponding to cytosine to be analyzed is cytosine among samples to be analyzed, a methylation frequency of cytosine to be analyzed may be also measured.

As a third method, there is a method in which, specimen-derived DNA is contacted with a reagent which modifies unmethylated cytosine and, thereafter, the DNA and a probe which can distinguish the presence or the absence of methylation of cytosine to be analyzed are hybridized and, thus, the presence or the absence of binding of the probe is investigated.

A DNA is first extracted from a mammal-derived specimen, for example, using a commercially available DNA extracting kit or the like.

When blood is used as a specimen, plasma or serum is prepared from the blood according to the conventional method, and free DNA (including a DNA derived from cancer cells such as pancreatic cancer cells and the like) contained in the prepared plasma or serum as a specimen is analyzed, whereby, a DNA derived from cancer cells such as pancreatic cancer cell can be analyzed while avoiding a hemocyte-derived DNA, and a sensitivity for detecting cancer cell such as pancreatic cancer cell, or a tissue containing it can be improved.

Then, after the extracted DNA is contacted with a reagent for modifying unmethylated cytosine, the DNA and a probe which can distinguish the presence or the absence of methylation of cytosine to be analyzed are hybridized and, thus, the presence or the absence of binding of the DNA with the probe is investigated. Cytosine to be analyzed may be selected from among cytosines in one or more nucleotide sequence(s) represented by 5'-CG-3' which is present in a nucleotide sequence of a promoter region, an untranslated region or a translated region (coding region) of Fibrillin2 gene.

Herein, examples of one or more nucleotide sequence(s) represented by CpG present in a nucleotide sequence of a promoter region, untranslated region or a translated region (coding region) of Fibrillin2 gene include a nucleotide sequence of a genomic DNA containing an exon 1 of human-derived Fibrillin2 gene and a promoter region located on a 5' upstream side thereof, more specifically, the nucleotide sequence represented by SEQ ID NO: 1 (corresponding to a sequence complementary to the nucleotide sequence represented by nucleotide numbers 118801 to 121000 of a nucleotide sequence described in Genbank Accession No. AC113387). In the nucleotide sequence represented by SEQ ID NO: 1, the nucleotide sequence of the exon 1 is shown by nucleotide numbers 1091 to 1345. Cytosine in a nucleotide sequence represented by CpG present in the nucleotide sequence represented by SEQ ID NO: 1, inter alia, cytosine in CpG present in a region in which CpGs are densely present in the nucleotide sequence represented by SEQ ID NO: 1 shows a high methylation frequency (i.e. hypermethylation status) in cancer cells such as pancreatic cancer cells. More specifically, examples of cytosine having a high methylation frequency in a pancreatic cancer cell include cytosines represented by nucleotide numbers 679, 687, 690, 699, 746, 773, 777, 783, 795, 799, 812, 823, 830, 834, 843 and the like in the nucleotide sequence of SEQ ID NO: 1.

It is better to design a probe used in the hybridization based on a nucleotide sequence containing cytosine to be analyzed in view of that cytosine which has not undergone methylation is converted into uracil, and cytosine which has undergone methylation is not converted into uracil. That is, a methylation-specific probe having a nucleotide sequence when methylated cytosine is contained [a nucleotide sequence in which cytosine at a position to be methylated (cytosine in CpG) still remains as cytosine, and unmethylated cytosine (cytosine not contained in CpG) is converted into uracil] or a nucleotide sequence complementary to such the nucleotide sequence, and a unmethylation-specific probe having a nucleotide sequence when cytosine is not methylated (a nucleotide sequence in which all cytosines are converted into uracil) or a nucleotide sequence complementary to such the nucleotide sequence are designed. Such the probe may be used after labeled, in order to facilitate analysis of the presence or the absence of binding of a DNA with the probe. Alternatively, a probe may be used by immobilizing on a carrier according to the conventional method. In this case, it is better to pre-label a DNA extracted from a mammal-derived specimen.

As a reagent for modifying unmethylated cytosine, bisulfite such as sodium bisulfite and the like can be used. Incidentally, in principle, a reagent which specifically modify only methylated cytosine can also be used.

In order that the extracted DNA is contacted with a reagent for modifying unmethylated cytosine, for example, after the DNA is first denaturated in an alkaline solution (pH 9 to 14), the DNA is treated with bisulfite such as sodium bisulfite (concentration in a solution: e.g. final concentration 3M) at 55° C. for around about 10 to 16 hours (overnight). Denaturation at 95° C. and reaction at 50° C. may be repeated 10 to 20 times to accelerate the reaction. In this case, unmethylated cytosine is converted into uracil and, on the other hand, methylated cytosine is not converted into uracil, but still remains as cytosine.

If necessary, by performing PCR using a DNA treated with bisulfite or the like as a template in the same manner as the second method, the DNA may be amplified in advance.

Then, a DNA treated with bisulfite or the like or the DNA pre-amplified by PCR Is hybridized with a probe which can distinguish the presence or the absence of methylation of cytosine to be analyzed. By comparing an amount of a DNA which binds with a methylation-specific probe, and an amount of a DNA which binds with an unmethylation-specific probe, a methylation frequency of cytosine to be analyzed can be measured.

More specifically, a probe for measuring a methylation frequency of Fibrillin2 gene can be designed as described above, for example, based on a nucleotide sequence containing one or more cytosine(s) in CpG present in a nucleotide sequence in a promoter region, an untranslated region or a translated region (coding region) of Fibrillin2 gene. For example, design can be performed based on a nucleotide sequence containing one or more cytosine(s) in CpG present in the nucleotide sequence represented by SEQ ID NO: 1, more specifically, cytosine(s) represented by nucleotide numbers 679, 687, 690, 699, 746, 773, 777, 783, 795, 799, 812, 823, 830, 834, 843 and the like in the nucleotide sequence represented by SEQ ID NO: 1. Examples of such the probe are shown below.

```
<Set 1>
Unmethylation-specific probe:
5'-TTGTTTTTGGAGTGTATGGGAATTTGTTGAG (SEQ ID NO: 8)
TTTTGT-3'

Methylation-specific probe:
5'-TCGTTTTCGGAGCGTACGGGAATTCGTCGAG (SEQ ID NO: 9)
TTTTGC-3'

<Set 2>
Unmethylation-specific probe:
5'-TTGGTTATGTAATGTGTATTGTTTGGGGTTG (SEQ ID NO: 10)
TTGGTT-3'

Methylation-specific probe:
5'-TCGGTTATGTAACGTGTATCGTTCGGGGTTG (SEQ ID NO: 11)
TCGGTT-3'
```

Hybridization can be performed according to the conventional method, for example, described in Sambrook J., Frisch E. F., Maniatis T., Molecular Cloning $2^{nd}$ edition, published by Cold Spring Harbor Laboratory press, and the like. Hybridization is usually performed under the stringent conditions. Herein, examples of the "stringent conditions" include the conditions under which a hybrid is formed at 45° C. in a solution containing 6×SSC (a solution containing 1.5M NaCl and 0.15M trisodium citrate is 10×SSC) and, thereafter, the hybrid is washed with 2×SSC at 50° C. (Molecular Biology, John Wiley and Sons, N.Y.(1989), 6.3.1-6.3.6), and the like. The salt concentration in the washing step can be selected, for example, from the conditions of 2×SSC and 50° C. (low stringency condition) to the conditions of 0.2×SSC and 50° C. (high stringency conditions). A temperature in a washing step can be selected, for example, from room temperature (low stringency condition) to 65° C. (high stringency condition). Alternatively, both of the salt concentration and temperature may be changed.

After such the hybridization is performed, a methylation frequency of cytosine to be analyzed (i.e. cytosine in CpG contained in a nucleotide sequence which is a basis for probe design) can be measured by comparing an amount of a DNA which binded with a methylation-specific probe, and an amount of a DNA which binded with an unmethylation-specific probe.

As a fourth method, there is a method in which, specimen-derived DNA is reacted with a restriction enzyme which can distinguish the presence or the absence of methylation of cytosine to be analyzed and, thereafter, the presence or the absence of digestion with the restriction enzyme is investigated.

A DNA is first extracted from a mammal-derived specimen, for example, using a commercially available DNA extracting kit or the like.

When blood is used as a specimen, plasma or serum is prepared from the blood according to the conventional method, and free DNA (including a DNA derived from cancer cells such as pancreatic cancer cells and the like) contained in the prepared plasma or serum as a specimen is analyzed, whereby, a DNA derived from cancer cells such as pancreatic cancer cell can be analyzed while avoiding a hemocyte-derived DNA, and a sensitivity for detecting cancer cell such as pancreatic cancer cell, or a tissue containing it can be improved.

Then, the extracted DNA is reacted with a restriction enzyme which can distinguish the presence or the absence of methylation of cytosine to be analyzed and, thereafter, the presence or the absence of digestion with the restriction enzyme is investigated. Cytosine to be analyzed may be selected from among cytosines in one or more nucleotide sequence (s) represented by 5'-CG-3' which is present in a nucleotide sequence of a promoter region, an untranslated region or a translated region (coding region) of Fibrillin2 gene.

Herein, examples of one or more nucleotide sequence(s) represented by CpG present in a nucleotide sequence of a promoter region, untranslated region or a translated region (coding region) of Fibrillin2 gene include a nucleotide sequence of a genomic DNA containing an exon 1 of human-derived Fibrillin2 gene and a promoter region located on a 5' upstream side thereof, more specifically, the nucleotide sequence represented by SEQ ID NO: 1 (corresponding to a sequence complementary to the nucleotide sequence represented by nucleotide numbers 118801 to 121000 of a nucleotide sequence described in Genbank Accession No. AC113387). In the nucleotide sequence represented by SEQ ID NO: 1, the nucleotide sequence of the exon 1 is shown by nucleotide numbers 1091 to 1345. Cytosine in a nucleotide sequence represented by CpG present in the nucleotide sequence represented by SEQ ID NO: 1, inter alia, cytosine in CpG present in a region in which CpGs are densely present in the nucleotide sequence represented by SEQ ID NO: 1 shows a high methylation frequency (i.e. hypermethylation status) in cancer cells such as pancreatic cancer cells. More specifically, examples of cytosine having a high methylation frequency in a pancreatic cancer cell include cytosines represented by nucleotide numbers 679, 687, 690, 699, 746, 773, 777, 783, 795, 799, 812, 823, 830, 834, 843 and the like in the nucleotide sequence of SEQ ID NO: 1.

The "restriction enzyme which can distinguish the presence or the absence of methylation of cytosine" (hereinafter, referred to as methylation-sensitive restriction enzyme in some cases) used in the method means a restriction enzyme which does not digest a recognition sequence containing methylated cytosine, and can digest a recognition sequence containing unmethylated cytosine. In the case of a DNA in which cytosine contained in a recognition sequence is methylated, the DNA is not cut even when a methylation-sensitive restriction enzyme is acted thereon and, on the other hand, in the case of a DNA in which cytosine contained in a recognition sequence is not methylated, the DNA is cut when a methylation-sensitive restriction enzyme is acted thereon. Examples of the methylation-sensitive enzyme include HpaII, BstUI, NarI, SacII and the like.

Examples of a method for investigating the presence or the absence of digestion with the restriction enzyme include a method for investigating the presence or the absence of amplification of a DNA (amplification product) by performing PCR, using as a template a DNA that was reacted with a restriction enzyme recognition sequence of which contains cytosine to be analyzed, and using a primer pair which can amplify a DNA containing recognition sequence that contains cytosine to be analyzed and not containing a recognition sequence for the restriction enzyme in addition to that recognition sequence. When cytosine to be analyzed is methylated, an amplification product is obtained. On the other hand, when cytosine to be analyzed is not methylated, an amplification product is not obtained. Like this, by comparing with an amount of the amplified DNA, a methylation frequency of cytosine to be analyzed can be measured. In cases where quantitative determination is required, amounts of the respective products may be compared by using Real Time PCR which is a PCR method capable of high-accuracy quantitation such that slight difference in gene dosage of about twice can be detected by real-time monitoring of PCR reaction product and analyzing kinetics. Methods of performing Real Time PCR include, for example, a method using a probe such as template-directed nucleic acid polymerase probe and a method using an intercalator such as SYBR Green. As apparatus and reagents for Real Time PCR, commercially available apparatus and reagents can be used.

For example, in the case of cytosine represented by the nucleotide number 42, 889 or 1083 in the nucleotide sequence represented by SEQ ID NO: 1, the cytosine is contained in a recognition sequence for NarI, and a methylation frequency of the cytosine can be measured by the aforementioned method.

Further, examples of other method for investigating the presence or the absence of digestion of the restriction enzyme include a method in which Southern hybridization is performed on a DNA which contains cytosine to be analyzed in a recognition sequence and has been reacted with a methylation-sensitive restriction enzyme, using, as a probe, a DNA which is derived from Fibrillin2 gene and does not contain a recognition sequence for the restriction enzyme, and a length of the hybridized DNA is investigated. When cytosine to be analyzed is methylated, a longer DNA is detected, as compared with the case where the cytosine is not methylated. By comparing an amount of the detected longer DNA and an amount of the shorter DNA, a methylation frequency of cytosine to be analyzed can be measured.

Using the aforementioned various methods, a methylation frequency of Fibrillin2 gene contained in a mammal-derived specimen is measured. By comparing the measured methylation frequency, and for example a methylation frequency (control) of Fibrillin2 gene contained in a healthy mammal-derived specimen which can be diagnosed not to have cancer cells such as pancreatic cancer cells, a cancerous state of the specimen is determined based on a difference obtained by the comparison. If a methylation frequency of Fibrillin2 gene contained in a mammal-derived specimen is higher as compared with a control (if Fibrillin2 gene is in a hypermethylation status as compared with a control), it can be determined that a cancerous state of the specimen is higher as compared with a control.

Herein, the "cancerous state" has the same meaning as that generally used in the art, specifically, for example, the cancerous state means a malignancy of the cell when a mammal-derived specimen is a cell, and means an amount of cancer cells existing in the tissue when a mammal-derived specimen is a tissue.

Expression of Fibrillin2 gene is lower in cancer cells such as pancreatic cancer cells than in a specimen such as a cell and a tissue derived from a healthy mammal. Since a methylation frequency of the gene is higher in cancer cells such as pancreatic cancer cells, the gene cannot be normally expressed and, as a result, an amount of an expression product of the gene (more specifically, an amount of a transcription product or an amount of a translation product) is decreased. Like this, the present assessing method and the like, in place of a methylation frequency, an index value having the correlation therewith (in the above case, the value is an amount of an expression product and an index value having the negative correlation) may be measured.

That is, in the present assessing method, a cancerous state of a specimen can be determined based on a difference obtained by measuring an index value (e.g. an amount of an expression product) having the correlation with a methylation frequency of Fibrillin2 gene contained in a mammal-derived specimen, and comparing the measured index value (e.g. an amount of an expression product) having the correlation with the aforementioned methylation frequency with a control.

Examples of a method for measuring an index value having the correlation with an methylation frequency of Fibrillin2 gene contained in a mammal-derived specimen in the first step of the present assessing method include a method for measuring an amount of a mRNA which is a transcription product of Fibrillin2 gene. For the measurement, the known methods such as a RT-PCR method, a Northern blotting method [Molecular cloning, Cold Spring harbor Laboratory (1989)], an in situ RT-PCR method [Nucleic acids Res., 21, 3159, 3166(1993)], an in situ hybridization method, and a NASBA method [Nucleic acid sequence-based amplification, nature, 350, 91-92 (1991)] may be used.

A sample containing a mRNA which is a transcription product of Fibrillin2 gene which is contained in a mammal-derived specimen may be prepared from the specimen by extraction, purification or the like according to the conventional method.

When the Northern blotting method is used for measuring an amount of a mRNA contained in the prepared sample, it is enough that a detecting probe contains Fibrillin2 gene or a part thereof (around about 100 bp to about 1000 bp oligonucleotides obtained by cutting Fibrillin2 gene with a restriction enzyme, or chemically synthesizing them based on a nucleotide sequence of Fibrillin2 gene), and is not particularly limited as far as it imparts specificity which can be detected under the detecting conditions used in hybridization with a mRNA contained in the sample.

When the RT-PCR method is used for measuring an amount of a mRNA contained in the prepared sample, it is enough that a primer used can specifically amplify only Fibrillin2 gene, and a region to be amplified and a number of nucleotides are not particularly limited. Examples of such the primer include primers (S: sense, A: antisense) and the like shown below. Using these primers, an amount of a transcription product may be also measured by the RT-PCR method as shown in Examples later. In cases where quantitative determination is required, amounts of the respective products may be compared by using Real Time PCR which is a PCR method capable of high-accuracy quantitation such that slight difference in gene dosage of about twice can be detected by real-time monitoring of PCR reaction product and analyzing kinetics. Methods of performing Real Time PCR include, for example, a method using a probe such as template-directed nucleic acid polymerase probe and a method using an intercalator such as SYBR Green. As apparatus and reagents for Real Time PCR, commercially available apparatus and reagents can be used.

S: 5'-GGCGAGGACAGCAGGAC-3'         (SEQ ID NO: 12)

A: 5'-TGATATTTGCCCACTGGAACA-3'     (SEQ ID NO: 13)

Examples of other method for measuring an index value having the correlation with a methylation frequency of Fibrillin2 gene which is contained in a mammal-derived specimen in the first step of the present assessing method include a method for measuring an amount of an Fibrillin2 protein which is a translation product of Fibrillin2 gene. For the measurement, the known methods such as an immunoblotting method, a separating method by immunoprecipitation, and an indirect competitive inhibiting method (ELISA method) described in Cell Technology Handbook, Yodosha, 207(1992), and the like, using a specific antibody (monoclonal antibody, polyclonal antibody) against a Fibrillin2 protein may be used.

Incidentally, a specific antibody against a Fibrillin2 protein can be prepared according to the conventional immunological method using the protein as an immune antigen.

Using the aforementioned various methods, an index value having the correlation with a methylation frequency of Fibrillin2 gene contained in a mammal-derived specimen is measured. By comparing an index value having the correlation with the measured methylation frequency, for example with an index value (control) having the correlation with the methylation frequency of the Fibrillin2 gene contained in a healthy mammal-derived specimen which can be diagnosed not to have cancer cells such as pancreatic cancer cells, based on a difference obtained by the comparison, a cancerous state of the specimen is determined. If an index value having the positive correlation with a methylation frequency of Fibrillin2 gene contained in a mammal-derived specimen is higher as compared with a control, or if an index value having the negative correlation therewith is lower as compared with the control (if Fibrillin2 gene is in a hypermethylation status as compared with a control), it can be determined that a cancerous state of the specimen is higher as is compared with a control.

A primer, a probe and a specific antibody which can be used in various methods for measuring a methylation frequency of Fibrillin2 gene or an index value having the correlation therewith in the present assessing method are useful as a reagent of a kit for detecting cancer cells such as pancreatic cancer cells. The present invention also provides a kit for detecting cancer cells such as pancreatic cancer cells which contains these primer, probe or specific antibody as a reagent, and a chip for detecting cancer cells such as pancreatic cancer cells which comprises the primer, the probe, the specific antibody or the like immobilized on a carrier, and the right scope of the present assessing method includes use in a form of the aforementioned detecting kit and detecting chip utilizing substantial principle of the method.

Expression of the gene is lower in cancer cells such as pancreatic cancer cells than in a specimen such as a cell and a tissue derived from a healthy mammal. On the other hand, as also shown in Examples later, by acting a substance inhibiting DNA methylation relating to Fibrillin2 gene on a cancer cell such as a pancreatic cancer cell and the like, an amount of an expression product of the gene can be increased. This means that a substance which can compensate reduction in an expression level of Fibrillin2 gene in cancer cells such as pancreatic cancer cells or function reduction accompanied therewith—for example, Fibrillin2 gene unmethylated (or in which methylation abnormality as recognized in cancer has not occurred), an expression product of the gene, a substance having the ability of promoting the expression of the gene (e.g. substance which inhibits DNA methylation relating to Fibrillin2 gene, a substance which reduces a methylation frequency of Fibrillin2 gene) and the like are useful in treating a cancer such as a pancreatic cancer and the like, and inhibiting canceration of a normal tissue such as pancreatic tissue.

For example, canceration would be inhibited by administering a substance which reduces a methylation frequency of Fibrillin2 gene to cells in a body of a mammal which can be diagnosed to be cancer. Further, for example, cancer cells such as pancreatic cancer cells is provided with a substance which inhibits DNA methylation relating to Fibrillin2 gene, whereby, cytosine in CpG present in a nucleotide sequence in a promoter region or a coding region of Fibrillin2 gene would be in a hypomethylation status like a normal tissue, an expression amount of a mRNA which is a transcription product of Fibrillin2 gene would be increase and, consequently, an expression amount of a Fibrillin2 protein which is a translation product of Fibrillin2 gene could be increased. Further, for example, by introducing into cancer cells such as pancreatic cancer cells Fibrillin2 gene or a cDNA comprising a nucleotide sequence encoding an amino acid sequence of a Fibrillin2 protein, an expression amount of a Fibrillin2 protein and the like in cancer cells such as pancreatic cancer cells could be increased.

That is, the present invention also provides (1) an anticancer agent, which comprises a substance having the ability of promoting the expression of Fibrillin2 gene as an active ingredient, wherein the active ingredient is formulated into a pharmaceutically acceptable carrier, and (2) an anti-cancer agent, which comprises a nucleic acid consisting of a nucleotide sequence encoding an amino acid sequence of Fibrillin2 gene as an active ingredient, wherein the active ingredient is formulated into a pharmaceutically acceptable carrier (hereinafter, collectively referred to as the present anti-cancer agent in some cases).

A dosage form of the present anti-cancer agent is not particularly limited as far as it is a conventional preparation, and such the preparation can be prepared, for example by incorporating an active ingredient into a pharmaceutically acceptable carrier such as a water-soluble solvent, a non-water-soluble solvent, a buffer, a solubilizer, an isotonic agent, and a stabilizer. If necessary, a supplementing agent such as an antiseptic, a suspending agent, and an emulsifying agent may be added. In addition, when administered parenterally (generally, preferably by an injection and the like), the anti-cancer agent can be used in the form of a conventional liquid preparation such as a solution and the like.

An effective amount of the present anti-cancer agent can be administered parenterally to mammals such as a human being (e.g. a cell in a body of a mammal which can be diagnosed to be cancer). Examples of a method for parenterally administering the agent include an injection (subcutaneously, intravenously, and locally) and the like.

A dose is different depending on age, sex and weight of a mammal to be administered, a degree of disease, a kind and an administration form of the present anti-cancer agent and the like and, usually, an active ingredient may be administered at an amount resulting in an intracellular level equivalent to such the concentration level that an active ingredient works effectively in a patient cell. Furthermore, the aforementioned dose per day can be administered once or by dividing into a few times.

Herein, examples of a method for introducing a nucleic acid comprising a nucleotide sequence encoding an amino acid sequence of Fibrillin2 into a cell include a gene introducing method utilizing a virus vector, a gene introducing method utilizing a non-virus vector (Nikkei Science, 1994, April, p 20-45, Experimental Medicine, Extra Edition, 12(15) (1994), Experimental Medicine Separate Volume "Fundamental Technique of Gene Therapy", Yodosha (1996)) and the like.

Examples of the former gene introducing method include a method for introducing the gene by incorporating a DNA encoding TR4 or mutant TR4 into DNA virus or RNA virus such as retrovirus, adenovirus, adeno-associated virus, herpesvirus, vacciniavirus, poxvirus, poliovirus, cinbisvirus and the like. In addition, examples of the gene introducing method utilizing a non-virus vector include a method for administering an expression plasmid directly into muscle (DNA vaccine method), a liposome method, a lipofectine method, a microinjection method, a calcium phosphate method, an electroporation method and the like.

In addition, examples of a method utilizing a nucleic acid comprising a nucleotide sequence encoding an amino acid sequence of Fibrillin2 as an active ingredient of a gene therapeutic as an anti-cancer agent include an in vivo method for introducing the nucleic acid directly into a body, an ex vivo method for taking out a particular cell of a human, introducing the nucleic acid into the cell outside a body, and returning the cell into a body (Nikkei Science, 1994, April, p 20-45, Monthly Pharmaceutical Affairs, 36(1), 23-48 (1994), Experimental Medicine, Extra Edition, 12(15)(1994)) and the like.

In the case of the former in vivo method, a nucleic acid comprising a nucleotide sequence encoding an amino acid sequence of Fibrillin2 can be administered via a suitable administration route depending on disease, symptom and the like. For example, the DNA can be administered to a pancreatic cancer cell, or intravenously, intraarterially, subcutaneously, intradermally or intramuscularly by an injection.

A dosage form of the gene therapeutic agent as an anti-cancer agent may be a suspension, or a liposome preparation such as a frozen agent, a centrifugation concentration frozen agent and the like in addition to an injectable. Such the preparation can be prepared by incorporating the gene (including a form of the gene of a vector type or a virus type, or a plasmid type) into a pharmaceutically acceptable carrier such as a water-soluble solvent, a non-water-soluble solvent, a buffer, a solubilizer, an isotonic agent, and a stabilizer. If necessary, a supplementing agent such as an antiseptic, a suspending agent, an emulsifying agent may be added. In addition, when parenterally administered (generally, preferably by an injection or the like), the anti-cancer agent can be used in the form of a conventional liquid preparation such as a solution and the like.

The present searching method is a method for searching a substance having the ability of promoting the expression of Fibrillin2 gene, and has (1) a first step of bringing a test substance into contact with a cancer cell, (2) a second step of measuring an amount of an expression product of Fibrillin2 gene contained in the cancer cell after the first step (1), and (3) a third step of determining the ability of promoting the expression of Fibrillin2 gene possessed by the test substance based on a difference obtained by comparing the measured amount of an expression product with a control.

A cancer cell in the first step of the present searching method is not particularly limited, and may be a cancer cell separated from a mammal-derived cancer tissue, or a mammal-derived cancer cell line which is established as a cell line. Examples of the mammal include human being, monkey, mouse, rat, hamster and the like. Preferable examples of the cancer include a pancreatic cancer and the like. Specifically, embodiments thereof include the known human-derived pancreatic cancer cell line such as BXPc3, HPAF-II, Capan-2, MiaPaCa-2, Hs766T, PANC-1, HPAC (all available from ATCC).

An amount of a cancer cell for bringing a test substance into contact with a cancer cell in the first step of the present searching method is usually about $10^4$ to $10^8$ cells, preferably about $10^5$ to $10^7$ cells. The concentration of a test substance is usually about 0.1 ng/ml to about 100 µg/ml, preferably about 1 ng/ml to about 50 µg/ml. A time period for bringing a test substance into contact with a cancer cell is usually 1 hour to around 5 days, preferably a few hours to around 2 days. A number of times for bringing a test substance into contact with a cancer cell may be once or plural times.

The environment under which a test substance is contacted with a cancer cell is preferably the environment under which vital activity of a cancer cell is maintained, for example, the environment under which the energy source of the cancer cell coexists. Specifically, it is advantageous that the first step is performed in a medium.

For measuring an amount of an expression product of Fibrillin2 gene contained in a cancer cell in the second step of the present searching method, the amount may be measured according to the aforementioned "method for measuring an index value having the correlation with a methylation frequency of Fibrillin2 gene contained in a mammal-derived specimen in the first step of the present assessing method" and the like.

For determining the ability of promoting the expression of Fibrillin2 gene possessed by a test substance based on a difference obtained by comparing an amount of an expression product measured in the second step of the present searching method with a control, as described above, the measured amount of an expression product is compared, for example, with an amount (control) of an expression product of Fibrillin2 gene when the concentration of a test substance for bringing a test substance into contact with a cancer cell in the first step of the present searching method is zero (that is, when a test substance is not contacted with a cancer cell), whereby, the ability of promoting the expression of Fibrillin2 gene possessed by a test substance is determined based on a difference obtained by the comparison. If an amount of an expression product of Fibrillin2 gene contained in a cancer cell which has been contacted with a test substance is higher when compared with a control (in this case, an amount of an expression product of Fibrillin2 gene contained in a cancer cell which has not been contacted with a test substance), it can be determined that the test substance has the ability of promoting the expression of Fibrillin2 gene. Of course, as a control, an amount of an expression product of Fibrillin2 gene when other test substance is contacted with a cancer cell may be used and, in this case, it is preferable that the ability of promoting expression for Fibrillin2 gene possessed by the other test substance is known in advance.

Like this, it is possible to search a substance having the ability of promoting the expression of Fibrillin2 gene. In addition, it is preferable that an amount of an expression product of Fibrillin2 gene contained in a specimen derived from a normal cell line such as a normal gastric cell line, or a healthy mammal which can be diagnosed not to have cancer cells such as pancreatic cancer cells is measured as a background or a control in both of the case where a test substance is contacted and the case where a test substance is not contacted.

EXAMPLES

The present invention will be explained in detail below by way of Examples, but the present invention is not limited by them.

Example 1

Test of Confirming Methylation Status of Fibrillin2 Gene in Pancreatic Cancer Cell Line Seven kinds of human-derived pancreatic cancer cell lines [BXPc3, HPAF-II, Capan-2, MiaPaCa-2, Hs766T, PANC-1 and HPAC (all obtained from ATCC)] were cultured to sub-confluent in a medium exclusively used for each cell line described in catalogs of ATCC (American Type Culture Collection), and thereafter about $1\times10^7$ cells were collected, respectively. Two kinds of immortal (normal) pancreatic ductal epithelial cells (HPDE-4/E6E7 and HPDE6-E6E7c7) [these are maintained and managed by Dr. Tsao (Ontario Cancer Institute and Department of Pathology, University of Toronto) and available from the researcher] were cultured to sub-confluent in Keratinocyte-SFM, liquid medium (Invitrogen) containing 50 U/ml of penicillin and 50 µg/ml of streptomycin, and thereafter about $1\times10^7$ cells were collected, respectively. 10-Fold volume of a SEDTA buffer [10 mM Tris/HCl (pH 8.0), 10 mM EDTA (pH 8.0), 100 mM NaCl] was added to the collected cells, and this was homogenized. To the resulting mixture were added proteinase K (Sigma) of 200 µg/ml and sodium dodecylsulfate of the amount to give a concentration of 1% (w/v), and this was shaken at 55° C. for about 16 hours. After completion of shaking, the mixture was treated by phenol [saturated with 1 MTris/HCl (pH8.0)]-chloroform extraction. The aqueous layer was recovered, and NaCl was added thereto to give a concentration of 0.5N, and this was ethanol-precipitated to recover the precipitates. The recovered precipitates were dissolved in a TE buffer (10 mM Tris, 1 mM EDTA, pH 8.0), and RNase A (Sigma) was added thereto to give a concentration of 40 µg/ml, followed by incubation at 37° C. for 1 hour. The incubated mixture was treated by phenol-chloroform extraction. The aqueous layer was recovered, NaCl was added thereto to give a concentration of 0.5N, and this was ethanol-precipitated to recover precipitates (genomic DNA). The recovered precipitates were rinsed with 70% ethanol to obtain a genomic DNA.

The resulting genomic DNA was digested with restriction enzyme BamHI and thereafter treated with sodium bisulfite according to the method described in Clark et al., Nucl. Acids. Res., 22, 2990-2997, 1994; Herman et al., Pro. Natl. Acad. Sci. USA, 93, 9821-9826, 1996. That is, the genomic DNA (0.2-1 µg) after the restriction-enzyme treatment was dissolved in distilled water to prepare 20 µl of a genomic DNA solution, about 2 µl of 6M sodium hydroxide was added thereto and, thereafter, the mixture was incubated at 37° C. for 15 minutes. To the mixture were added 0.6 mM hydroquinone (Sigma) to give a concentration of 0.5 mM and sodium bisulfite (Sigma) to give a concentration of 3.1 M, and this was incubated with 15 cycles of temperature maintenance, each cycle being 30 seconds at 95° C., then 15 minutes at 50° C. A DNA was purified from the incubated solution using Wizard DNA clean up system (Promega). The purified DNA was dissolved in 50 µl of a TE buffer, and sodium hydroxide was added thereto to give a concentration of 0.3 M, thereafter, the mixture was allowed to stand at room temperature for 5 minutes. Then, the stood mixture was ethanol-precipitated to recover precipitates (DNA). The recovered precipitates were suspended in 20 μl of a TE buffer.

The resulting DNA was used as a template and PCR was performed using unmethylation-specific primers U1 and U2, or methylation-specific primers M1 and M2 shown below. When unmethylation-specific primers U1 and U2 are used, a 171 bp DNA is amplified, said DNA comprising a nucleotide sequence arising from bisulfite treatment of DNA which had comprised the nucleotide sequence represented by nucleotide numbers 677 to 847 in the nucleotide sequence represented by SEQ ID NO: 1. While when methylation-specific primers M1 and M2 are used, a 168 bp DNA is amplified, said DNA comprising a nucleotide sequence arising from bisulfite treatment of DNA which had comprised the nucleotide sequence represented by nucleotide numbers 680 to 817 in the nucleotide sequence represented by SEQ ID NO: 1.

```
<Unmethylation-specific primer>
U1: 5'-TATGGGAATTTGTTGAGTTTTGT-3'    (SEQ ID No: 2)
U2: 5'-AACCAACAACCCCAAACA-3'          (SEQ ID No: 3)

<Methylation-specific primer>
M1: 5'-GGGAATTCGTCGAGTTTTGC-3'       (SEQ ID No: 4)
M2: 5'-AACCGACAACCCCGAACG-3'          (SEQ ID No: 5)
```

To verify specificity of the unmethylation-specific primer and methylation-specific primer, genomic DNA (DNA1) was first extracted from immortal (normal) pancreatic ductal epithelial cell (HPDE-4/E6E7) by a conventional method, and part of the DNA was treated with methylase SssI (NEB) to methylate all 5'-CG-3' (s) contained in the genomic DNA (DNA2). Regarding the DNA1 and DNA2, unmethylation-specific PCR and methylation-specific PCR were performed.

A reaction solution for PCR was used which was obtained by mixing 25 ng of a DNA as a template, each 1 μl of 20 pmol/μl aforementioned primer solutions, 2.5 μl of 2 mM dNTP, 2.5 μl of 10× buffer (100 mL Tris-HCl pH 8.3, 500 mM KCl, 20 mM MgCl$_2$) and 0.2 μl of a 5 U/μl thermostable DNA polymerase, and adding sterilized ultrapure water thereto to an amount of solution of 25 μl. When the aforementioned unmethylation-specific primer was used, PCR was performed at the conditions under which the reaction solution was retained at 95° C. for 10 minutes, and 32 cycles of temperature maintenance were performed, each cycle was 30 seconds at 95° C., 30 seconds at 59° C. and 30 seconds at 72° C. In addition, when the aforementioned methylation-specific primer was used, PCR was performed at the conditions under which the reaction solution was retained at 95° C. for 10 minutes, and 32 cycles of temperature maintenance were performed, each cycle was 30 seconds at 95° C., 30 seconds at 62° C. and 30 seconds at 72° C. In any case, after PCR was performed, a reaction solution of PCR containing the amplification product was subjected to 2% agarose gel electrophoresis.

Results are shown in FIG. 1. In the case of human-derived immortal (normal) pancreatic ductal epithelial cell lines (HPDE-4/E6E7 and HPDE6-E6E7c7), when an unmethylation-specific primer was used (lane U), a band of the amplified DNA was recognized, and when a methylation-specific primer was used (lane M), a band of the amplified DNA was not detected. Therefore, in the case of human-derived immortal (normal) pancreatic ductal epithelial cell lines (HPDE-4/E6E7 and HPDE6-E6E7c7), it was determined that at least cytosines represented by nucleotide numbers 679, 687, 690, 699, 830, 834 and 843, respectively, of the nucleotide sequence represented by SEQ ID NO: 1 were not methylated.

On the other hand, in the case of seven kinds of pancreatic cancer cell lines (BXPc3, HPAF-II, Capan-2, MiaPaCa-2, Hs766T, PANC-1 and HPAC), when an unmethylation-specific primer was used (lane U), a band of the amplified DNA was not detected, and when a methylation-specific primer was used (lane M), a band of a DNA was recognized. Therefore, under that condition, it was determined that cytosines represented by nucleotide numbers 687, 690, 699, 830, 834 and 843, respectively, of the nucleotide sequence represented by SEQ ID NO: 1 were methylated.

Example 2

Test of Confirming Methylation Status of Fibrillin2 Gene in Pancreatic Cancer Tissues To each of 12 specimens (Case 1 to Case 12) of pancreatic cancer tissues and the surrounding pancreatic normal tissues (obtained from patients with their informed consent), 10-Fold volume of a SEDTA buffer [10 mM Tris/HCl (pH 8.0), 10 mM EDTA (pH 8.0), 100 mM NaCl] was added, and this was homogenized. To the resulting mixture were added proteinase K (Sigma) of 200 μg/ml and sodium dodecylsulfate of the amount to give a concentration of 1% (w/v), and this was shaken at 55° C. for about 16 hours. After completion of shaking, the mixture was treated by phenol [saturated with 1M Tris/HCl (pH 8.0)]-chloroform extraction. The aqueous layer was recovered, and NaCl was added thereto to give a concentration of 0.5N, and this was ethanol-precipitated to recover the precipitates. The recovered precipitates were dissolved in a TE buffer (10 mM Tris, 1 mM EDTA, pH 8.0), and RNase A (Sigma) was added thereto to give a concentration of 40 μg/ml, followed by incubation at 37° C. for 1 hour. The incubated mixture was treated by phenol-chloroform extraction. The aqueous layer was recovered, NaCl was added thereto to give a concentration of 0.5N, and this was ethanol-precipitated to recover precipitates (genomic DNA). The recovered precipitates were rinsed with 70% ethanol to obtain a genomic DNA.

The resulting genomic DNA was digested with restriction enzyme BamHI and thereafter treated with sodium bisulfite according to the method described in Clark et al., Nucl. Acids. Res., 22, 2990-2997, 1994; Herman et al., Pro. Natl. Acad. Sci. USA, 93, 9821-9826, 1996. That is, the genomic DNA (0.2-1 μg) after the restriction-enzyme treatment was dissolved in distilled water to prepare 20 μl of a genomic DNA solution, about 2 μl of 6M sodium hydroxide was added thereto and, thereafter, the mixture was incubated at 37° C. for 15 minutes. To the mixture were added 0.6 mM hydroquinone (Sigma) to give a concentration of 0.5 nM and sodium bisulfite (Sigma) to give a concentration of 3.1 M, and this was incubated with 15 cycles of temperature maintenance, each cycle being 30 seconds at 95° C., then 15 minutes at 50° C. A DNA was purified from the incubated solution using Wizard DNA clean up system (Promega). The purified DNA was dissolved in 50 μl of a TE buffer, and sodium hydroxide was added thereto to give a concentration of 0.3 M, thereafter, the mixture was allowed to stand at room temperature for 5 minutes. Then, the stood mixture was ethanol-precipitated to recover precipitates (DNA). The recovered precipitates were suspended in 20 μl of a TE buffer.

The resulting DNA was used as a template and PCR was performed using unmethylation-specific primers U1 and U2, or methylation-specific primers M1 and M2 shown below. When unmethylation-specific primers U1 and U2 are used, a 171 bp DNA is amplified, said DNA comprising a nucleotide sequence arising from bisulfite treatment of DNA which had comprised the nucleotide sequence represented by nucleotide numbers 677 to 847 in the nucleotide sequence represented by SEQ ID NO: 1. While when methylation-specific primers M1 and M2 are used, a 168 bp DNA is amplified, said DNA comprising a nucleotide sequence arising from bisulfite treatment of DNA which had comprised the nucleotide sequence represented by nucleotide numbers 680 to 847 in the nucleotide sequence represented by SEQ ID NO: 1.

```
<Unmethylation-specific primer>
U1:  5'-TATGGGAATTTGTTGAGTTTTGT-3'    (SEQ ID No: 2)
U2:  5'-AACCAACAACCCCAAACA-3'         (SEQ ID No: 3)

<Methylation-specific primer>
M1:  5'-GGGAATTCGTCGAGTTTTGC-3'       (SEQ ID No: 4)
M2:  5'-AACCGACAACCCCGAACG-3'         (SEQ ID No: 5)
```

Specificity of the unmethylation-specific primer and methylation-specific primer were verified, as described in Example 1, in genomic DNA (DNA1) of immortal (normal) pancreatic ductal epithelial cell (HPDE-4/E6E7) and in part of the DNA treated with methylase SssI (NEB) resulting in the genomic DNA (DNA2).

A reaction solution for PCR was used which was obtained bar mixing 25 ng of a DNA as a template, each 1 μl of 20 pmol/μl aforementioned primer solutions, 2.5 μl of 2 mM dNTP, 2.5 μl of 10× buffer (100 mL Tris-HCl pH 8.3, 500 mM KCl, 20 mM MgCl$_2$) aid 0.2 μl of a 5 U/μl thermostable DNA polymerase, and adding sterilized ultrapure water thereto to an amount of solution of 25 μl. When the aforementioned unmethylation-specific primer was used, PCR was performed at the conditions under which the reaction solution was retained at 95° C. for 10 minutes, and 32 cycles of temperature maintenance were performed, each cycle was 30 seconds at 95° C., 30 seconds at 59° C. and 30 seconds at 72° C. In addition, when the aforementioned methylation-specific primer was used, PCR was performed at the conditions under which the reaction solution was retained at 95° C. for 10 minutes, and 32 cycles of temperature maintenance were performed, each cycle was 30 seconds at 95° C., 30 seconds at 62° C. and 30 seconds at 72° C. In any case, after PCR was performed, a reaction solution of PCR containing the amplification product was subjected to 2% agarose gel electrophoresis.

Results are shown in FIG. 2. In the case of 12 specimens of human-derived pancreatic normal tissues, when an unmethylation-specific primer was used (lane U), a band of the amplified DNA was recognized, and when a methylation-specific primer was used (lane M), a band of the amplified DNA was not detected. Therefore, in the case of human-derived pancreatic normal tissues, it was determined that at least cytosines represented by nucleotide numbers 679, 687, 690., 699, 830, 834 and 843, respectively, of the nucleotide sequence represented by SEQ ID NO: 1 were not methylated. In the case of 9 specimens among the 12 specimens of pancreatic cancer tissues, in addition to a band amplified when an unmethylation-specific primer was used (lane U), a band of a DNA was also recognized when a methylation-specific primer was used (lane M). Therefore, under that condition, it was determined that at least cytosines represented by nucleotide numbers 687, 690, 699, 830, 834 and 843, respectively, of the nucleotide sequence represented by SEQ ID NO: 1 were methylated owing to canceration of part of the tissue.

Example 3

Test of Confirming Expression Status of Fibrillin2 Gene in Pancreatic Cancer Cell Line and Effect of Methylation Inhibitor on Expression of the Gene seven kinds of human-derived pancreatic cancer cell lines (BXPc3, HPAF-II, Capan-2, MiaPaCa-2, Hs766T, PANC-1 and HPAC) and immortal (normal) pancreatic ductal epithelial cells lines (HPDE-4/E6E7 and HPDE6-E6E7c7) were cultured to 70% confluent in an exclusively used medium, and thereafter, each cell was corrected. 1 ml of an ISOGEN solution (Nippon Gene) was mixed with collected each cell (wet weight about 100 mg), this was homogenized, and 0.2 ml of chloroform was added thereto to suspend them. After suspending, the mixture was centrifuged (4° C., 15000×g, 15 minutes) to recover the supernatant. 0.5 ml isopropanol was added to the recovered supernatant to suspend them, and the suspension was centrifuged (4° C., 15000×g, 15 minutes) to recover the precipitates (RNA). The recovered precipitates were rinsed with 75% ethanol, and dissolved in DEPC (diethyl pyrocarbonate)-treated water.

Two kinds of human-derived pancreatic cancer cell lines (PANC-1 and HPAC) were seeded at a density of about 6×10$^5$ cells/10 cm plate, and cultured using an exclusively used medium. On the first day after seeding, 5-aza-2'-deoxytidine (manufactured by Sigma) (hereinafter, referred to as 5 Aza-dC) which is a methylation inhibitor was added to a medium to give the concentration of 0.5 or 1 μM. Twenty four hours after addition of 5 Aza-Dc, the medium was exchanged with the aforementioned medium to which no 5 Aza-dC was added, and culturing was continued. Then, on the third day after seeding, 5 Aza-dC was added to the medium similarly. On the fourth day after seeding, cells were recovered, and RNA was extracted and recovered from the recovered cells according to the same manner as described above.

The thus obtained 3 μg of RNA was treated with DNaseI (Ambion), and this was used as a template and Superscript II (Invitrogen) was used to synthesize a cDNA according to a protocol attached to the enzyme. By performing Real Time PCR using the synthesized cDNA as a template and using Fibrillin2 S and Fibrillin2 A shown below as a primer pair, a DNA derived from a mRNA of Fibrillin2 gene was amplified. Thereupon, as a control by performing PCR using the aforementioned cDNA as a template and using GAPDH S and GAPDH A solution below as a primer pair, a DNA derived from a mRNA of a Glyceraldehyde 3-phosphate dehydrogenase (GAPDH) gene was amplified.

```
<Primer (S: sense, A: antisense)>
Fibrillin2 S:
5'-GGCGAGGACAGCAGGAC-3'          (SEQ ID NO: 12)

Fibrillin2 A:
5'-TGATATTTGCCCACTGGAACA-3'      (SEQ ID NO: 13)

GAPDH S:
5'-AGGTGAAGGTCGGAGTCAACG-3'      (SEQ ID NO: 14)

GAPDH A:
5'-AGGGGTCATTGATGGCAACA-3'       (SEQ ID NO: 15)
```

A reaction solution of PCR was used which was obtained by mixing 50 ng of a cDNA as a template, each 1 μl of two kinds of 10 pmol/μl aforementioned primer solution, 4 μl of 2.5 mM dNTP, 4 µl of 5 mM dUTP, 5 µl of 10×SYBR Green PCR Buffer, 6 µl of 25 mM MgCl$_2$ and 0.3 µl of a 5 U/µl thermos table DNA polymerase (AmpliTaq Gold), 0.5 µl of AmpEraseUNG and adding sterilized ultrapure water thereto to an amount of solution of 50 µl. Real Time PCR was conducted by using iCycler Thermal Cycler (Bio-Rad Laboratories). When a DNA derived from mRNA of Fibrillin2 gene and GAPDH gene was amplified, after the reaction solution was retained at 95° C. for 10 minutes, Real Time PCR was performed at the conditions under which each cycle was 30 seconds at 95° C., 30 seconds at 59° C. and 30 seconds at 72° C. to quantitate Fibrillin2 gene and GAPDH gene.

The results are shown in FIG. 3 and FIG. 4. In the case of human-derived immortal (normal) pancreatic ductal epithelial cells lines (HPDE-4/E6E7 and HPDE6-E6E7c7), a DNA derived from a mRNA of Fibrillin2 gene was detected, while in any case of seven kinds of pancreatic cancer cell lines, the DNA was not detected. That is, in human-derived immortal (normal) pancreatic ductal epithelial cells lines (HPDE-4/E6E7 and HPDE6-E6E7c7), expression of Fibrillin2 gene was confirmed, while in any of seven pancreatic cancer cell lines, expression of Fibrillin2 gene was not recognized.

In the case of PANC-1 and HPAC cultured in the presence of 0.5 µM or 1 µM 5Aza-dC, a DNA derived from a mRNA of Fibrillin2 gene was detected. Meanwhile, a DNA derived from a mRNA of GAPDH gene was detected similarly, in the case of immortal (normal) pancreatic ductal epithelial cell lines (HPDE-4/E6E7 and HPDE6-E6E7c7), in the case of pancreatic cancer cell lines PANC-1 and HPAC cultured in the absence of 5Aza-dC, and in the case of PANC-1 and HPAC cultured in the presence of 0.5 µM or 1 µM 5Aza-dC. That is, in the case of pancreatic cancer cell lines PANC-1 and HPAC, expression of Fibrillin2 gene was recognized in the presence of a methylation inhibitor.

From the foregoing results, it was made clear that the aforementioned methylation in a pancreatic cancer cell line is inhibited by a methylation inhibitor, and Fibrillin2 gene is expressed in the presence of methylation inhibitor.

INDUSTRIAL APPLICABILITY

The present invention can provide a method for assessing cancerous state of a mammal-derived specimen.

Free Text in Sequence Listing
SEQ ID NO: 2
  Designed oligonucleotide primer for PCR
SEQ ID NO: 3
  Designed oligonucleotide primer for PCR
SEQ ID NO: 4
  Designed oligonucleotide primer for PCR
SEQ ID NO: 5
  Designed oligonucleotide primer for PCR
SEQ ID NO: 6
  Designed oligonucleotide primer for PCR
SEQ ID NO: 7
  Designed oligonucleotide primer for PCR
SEQ ID NO: 8
  Designed oligonucleotide for probe
SEQ ID NO: 9
  Designed oligonucleotide for probe
SEQ ID NO: 10
  Designed oligonucleotide for probe
SEQ ID NO: 11
  Designed oligonucleotide for probe
SEQ ID NO: 12
  Designed oligonucleotide primer for PCR
SEQ ID NO: 13
  Designed oligonucleotide primer for PCR
SEQ ID NO: 14
  Designed oligonucleotide primer for PCR
SEQ ID NO: 15
  Designed oligonucleotide primer for PCR

The invention claimed is:

1. A method for assessing a cancerous state of a mammal-derived pancreatic specimen, which comprises:
   (1) measuring a methylation frequency of Fibrillin2 gene contained in a mammal-derived pancreatic specimen or an index value having the correlation therewith, and
   (2) determining a cancerous state of the specimen based on a difference obtained by comparing the measured methylation frequency or the index value having the correlation therewith, with a control.

2. The assessing method according to claim 1, wherein the specimen is cells.

3. The assessing method according to claim 1, wherein the specimen is a tissue.

4. A method for assessing a cancerous state of a mammal-derived pancreatic specimen, which comprises:
   (1) of measuring a methylation frequency of Fibrillin2 gene contained in the mammal-derived pancreatic specimen, and
   (2) of determining a cancerous state of the specimen based on a difference obtained by comparing the measured methylation frequency with a control.

5. The assessing method according to claim 1, wherein the specimen is cells, and the cancerous state of the specimen is a malignancy of the cells.

6. The assessing method according to claim 4, wherein the specimen is cells, and the cancerous state of the specimen is a malignancy of the cells.

7. The assessing method according to claim 1, wherein the specimen is a tissue, and the cancerous state of the specimen is an amount of cancer cells existing in the tissue.

8. The assessing method according to claim 4, wherein the specimen is a tissue, and the cancerous state of the specimen is an amount of cancer cells existing in the tissue.

9. The assessing method according to claim 8, wherein the tissue is a pancreatic tissue, and the cancer is pancreatic cancer.

10. The assessing method according to claim 1 or 4, wherein the methylation frequency of a gene is a methylation frequency of cytosine in one or more nucleotide sequence(s) represented by 5'-CG-3' present in a nucleotide sequence of a promoter region, an untranslated region or a translated region of the gene.

11. The assessing method according to claim 10, wherein the tissue is a pancreatic tissue, and the cancer is pancreatic cancer.

12. The assessing method according to claim 1 or 4, wherein the methylation frequency of a gene is a methylation frequency of cytosine in one or more nucleotide sequence(s) represented by 5'-CG-3' present in a nucleotide sequence of a promoter region in the gene.

13. The assessing method according to claim 1 or 4, wherein the methylation frequency of a gene is a methylation frequency of cytosine in one or more nucleotide sequence(s) represented by 5'-CG-3' present in a nucleotide sequence of an untranslated region or a translated region of the gene.

14. The assessing method according to claim 1, wherein the methylation frequency of a gene is a methylation frequency of cytosine in one or more nucleotide sequence(s) represented by 5'-CG-3' present in the nucleotide sequence represented by SEQ ID No: 1.

15. The assessing method according to claim 14, wherein the tissue is a pancreatic tissue, and the cancer is pancreatic cancer.

16. A method for assessing a cancerous state of a mammal-derived pancreatic specimen, which comprises:
   (1) of measuring an index value having the correlation with a methylation frequency of Fibrillin2 gene contained in the mammal-derived pancreatic specimen, and
   (2) of determining a cancerous state of the specimen based on a difference obtained by comparing the index value having the correlation with the measured methylation frequency with a control.

17. The assessing method according to claim 16, wherein the index value having the correlation with a methylation frequency of Fibrillin2 gene is an amount of an expression product of the Fibrillin2 gene.

18. The assessing method according to claim 17, wherein the amount of an expression product of Fibrillin2 gene is an amount of a transcription product of the gene.

19. The assessing method according to claim 17, wherein the amount of an expression product of Fibrillin2 gene is an amount of a translation product of the gene.

* * * * *

SEQUENCE LISTING

<160> NUMBER OF SEQ ID NOS: 15

<210> SEQ ID NO 1
<211> LENGTH: 2200
<212> TYPE: DNA
<213> ORGANISM: Homo sapiens

<400> SEQUENCE: 1

```
cctcgccccc tccagccggc cccccgggcc cctcctctcg gcgcccggac cttggccctc        60
cctctccttt cccacttctc tctttgccct aacttcgccc ccatcccccg ctcatttcct       120
ctcgcacccg ggctcgccaa tccctctttc caagtccctc ttccagcccg gccttcctct       180
cgggttcgcc cccttctcc ccaatctccg tcctcttccc tccttcgcc ctccccccct         240 tccttcctct tccctcacc caaccctggt tccctcgtt cctcagtccc gatctctccc         300
ttactctgtc cccgcccact ctgcgccggc ctctcagtcc gggttgagcc ccacgtgtgg       360
acggccgcgc ccccactgac agccgccgcc cgccggcccg ccccgcgccc cgccgggcct      420
ctaaaacccc cgccgccgcg cctccaccgc cgcatcttct ccagcgccca gcctcccgcc      480
ctctctcttg ctggccgcac gccccggccc cgcgcacctc cgcccggctc cgcagccgct      540
acccgcgctt cgttgccctg tgggactccg agcgagcccg gagggaaccc tcctcttctt      600 ctggggggcga cttttgtttg cttgcctgtt tctttctggt gacttttgca gctttccaat     660
```

-continued

```
atccgtcttc ggagcgcacg ggaatccgcc gagctctgcg tgcaggccct ttttctttt      720 gaggttcaca ttttttgaaa ttttacgcca gggcttttgt aatttcctcc cccgcccgct      780
gacggtcctg gagtcgctcg gggctttagg ccggttatgc aacgtgtacc gctcggggct      840
gccggctgca cctccgccgc gcctcgccgc tcactgcgct agacccggcg ccccgcgtct      900
cgcttcgcgg gcagtcaggg ggccggcgct ctgtcgaggt ctccagctag agcagggagc      960
ccgagcccga gggagtcccc ggagccgacg aagggcttat tagaccctga ctctttctg     1020 aggcgcgcag attttgtctt tgatcactcc ctctccgcgg gtctacggcc gcgcgctttc     1080
ggcgccggcg atggggagaa gacggaggct gtgtctccag ctctacttcc tgtggctggg     1140
ctgtgtggtg ctctgggcgc agggcacggc cggccagcct cagcctcctc cgcccaagcc     1200
gccccggccc cagccgccgc cgcaacaggt tcggtccgct acagcaggct ctgaaggcgg     1260
gtttctagcg cccgagtatc gcgaggaggg tgccgcagtg gccagccgcg tccgccggcg     1320
aggacagcag gacgtgctcc gagggtaagt gggcaagcgg ctccgcacct agggctccgg     1380
cttgggggag gggggaatcc tcagtttggc ggctttctgg cccactccgt cccagaccct     1440
ttagctggag cctagagctg cagcccctt tgccagaata ccaaagacc cccaggagcg      1500 cgtccccctt ttccttccca accccgcagc tcagcgggcg gaaagccctc tctccggggg     1560
ttgggcggcg ggtggttagg gggtccaggg gtgccgatcg cagagcgtgt gcagagctcg     1620
cgctgcggga acaggttctg aatgtccggc ggcaggcggg cctgggtccg cctgctgcag     1680
gggccagaga agcctgcttg ctccccacgt cggggccgcc gtcgtgagc cttttgtttg     1740 aggacgtgtg cagggttcac agctcacctt ctcatcgtca acccgagcgc tccaccttgc     1800
gacgcgcttt ccttgacacg tcggggccaa agtaacagtt gaccaaggag gaatggattt     1860
gggaaggagg gcaaggattc tttggaacgg aatggtccct tgttctctg catctggaag      1920 ctagaatagt agcaaattat atgtttccat gcctcttttc gcccttaaa aaggcaggca     1980 agggacgaca gatgaaaggc agtgtttaga catttctgac cctcctgcat tccagcatct     2040
agctcttttg cttccacgtc tgcctcccga tctccaataa tttgaagtgt aattttgatt     2100
tgtttgttgt cctgaaatct actcgctcgg ggcattgctt acgaagaccg tttatatgtt     2160
gctgcatccc tctacctatc tgttacgtga ccgcgcttgt                           2200
```

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tatgggaatt tgttgagttt tgt                                              23

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaccaacaac cccaaaca                                                    18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggaattcgt cgagttttgc                                              20

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaccgacaac cccgaacg                                                18

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tagttggagt ttagagttgt a                                            21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cttctctaac ccctacaac                                               19

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8 ttgttttttgg agtgtatggg aatttgttga gttttgt                          37

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tcgttttcgg agcgtacggg aattcgtcga gttttgc                           37

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ttggttatgt aatgtgtatt gtttggggtt gttggtt                              37

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tcggttatgt aacgtgtatc gttcggggtt gtcggtt                              37

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcgaggaca gcaggac                                                    17

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgatatttgc ccactggaac a                                               21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aggtgaaggt cggagtcaac g                                               21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggggtcatt gatggcaaca                                                 20